United States Patent [19]
Gennetti

[11] Patent Number: 6,042,604
[45] Date of Patent: Mar. 28, 2000

[54] EXTREMITY SUPPORT APPARATUS AND METHOD

[76] Inventor: Debra Gennetti, 111 Geiger Dr., Tewksbury, Mass. 01876

[21] Appl. No.: 09/015,599

[22] Filed: Jan. 30, 1998

[51] Int. Cl.[7] .................................................. A61F 7/00
[52] U.S. Cl. ..................... 607/108; 607/114; 607/112; 5/636; 5/645
[58] Field of Search .................. 5/630–652, 421, 5/655.9, 948–953; 607/104, 108–112, 114; 128/882, 877; 602/23, 12; 606/240

[56] References Cited

U.S. PATENT DOCUMENTS

| | | | |
|---|---|---|---|
| 3,955,565 | 5/1976 | Johnson, Jr. ............................. | 128/882 |
| 3,967,335 | 7/1976 | Rhoads ..................................... | 5/338 |
| 4,288,879 | 9/1981 | Pate ........................................... | 5/431 |
| 4,505,270 | 3/1985 | Miles ........................................ | 128/882 |
| 4,683,601 | 8/1987 | Lagin ........................................ | 5/431 |
| 5,048,542 | 9/1991 | Murray ..................................... | 128/889 |
| 5,185,897 | 2/1993 | Van Laanen ............................. | 5/455 X |
| 5,383,920 | 1/1995 | Sikes ......................................... | 607/108 X |
| 5,388,295 | 2/1995 | Sarkozi ..................................... | 5/630 |
| 5,400,449 | 3/1995 | Satto ......................................... | 5/631 |
| 5,566,682 | 10/1996 | Yavitz ....................................... | 128/845 |
| 5,664,271 | 9/1997 | Bellavance ............................... | 5/632 |

*Primary Examiner*—John P. Lacyk
*Assistant Examiner*—Ryan Carter
*Attorney, Agent, or Firm*—Bromberg & Sunstein LLP

[57] ABSTRACT

An apparatus for supporting an extremity of a person includes a body having a recessed support surface for supporting the extremity, and a flap connected to the support surface. The body has a fastener that couples with a coupler on the flap to define a re-closable chamber. An ice bag or other similar heat absorbing apparatus may be secured within the chamber, thereby enabling the apparatus to both support the extremity and provide the anti-inflammatory function of the ice bag. The body, which may be crescent shaped, may include an interior for containing stuffing material. Both the body and the flap may be manufactured from the same fabric material.

17 Claims, 3 Drawing Sheets

EXTREMITY SUPPORT APPARATUS AND METHOD

FIELD OF THE INVENTION

The invention generally relates to body support structures and, more particularly, the invention relates to supporting bodily extremities when a person is laying on his/her side.

BACKGROUND OF TH INVENTION

When a patient is recovering from breast surgery (e.g., breast biopsy surgery or breast augmentation surgery), it often is recommended that such patient sleep on her side and support her breast with a supporting apparatus such as, for example, a pillow. This should reduce pain during sleep and facilitate the healing process. Moreover, to reduce post-operative breast swelling, it also commonly is recommended that the patient apply a heat absorbing apparatus (e.g., an ice bag or cold compress) to the breast when laying on her side. Use of a heat absorbing apparatus when in such a position, however, typically is awkward and cumbersome, especially when used with a breast supporting apparatus.

Accordingly, it would be desirable to provide an apparatus and method that facilitates the use of both a heat absorbing apparatus and a breast supporting apparatus when a patient is recovering from breast surgery.

SUMMARY OF TH INVENTION

In accordance with one aspect of the invention, an apparatus for supporting an extremity (e.g., a breast) of a person includes a body having a recessed support surface for supporting the extremity, and a flap connected to the support surface. The body has a fastener that couples with a coupler on the flap to define a re-closable chamber. An ice bag or other similar heat absorbing apparatus may be secured within the chamber, thereby enabling the apparatus to both support the extremity and provide the anti-inflammatory function of the ice bag. The body, which preferably is crescent shaped, may include an interior for containing stuffing material. In preferred embodiments, both the body and the flap are manufactured from the same fabric material. In other embodiments, the fastener is VELCRO™ and the coupler is a strip of fabric that couples with the VELCRO™. The body may include a back surface that is larger than a front surface, and a substantially flat bottom surface for supporting the body. In preferred embodiments, the flap is manufactured so that the, chamber is expandable from a substantially zero volume to a volume that is large enough to accept a conventional ice bag or other heat absorbing apparatus.

In accordance with other aspects of the invention, a method of supporting a breast of at person includes the steps of laying the person on her side against a base surface, providing a supporting pillow with a body and a flap that cooperate to define a reclosable chamber, opening the chamber and placing a heat absorbing apparatus within the chamber, closing the chamber to substantially secure the heat absorbing apparatus within the chamber, and positioning the pillow under the breast so that the flap contacts the breast. When supporting the breast, the supporting pillow is supported by the base surface.

BRIEF DESCRIPTION OF THE DRAWINGS

The foregoing and other objects and advantages of the invention will be appreciated more fully from the following further description thereof with reference to the accompanying drawings wherein.

DESCRIPTION OF ILLUSTRATIVE EMBODIMENTS

Figure 1:
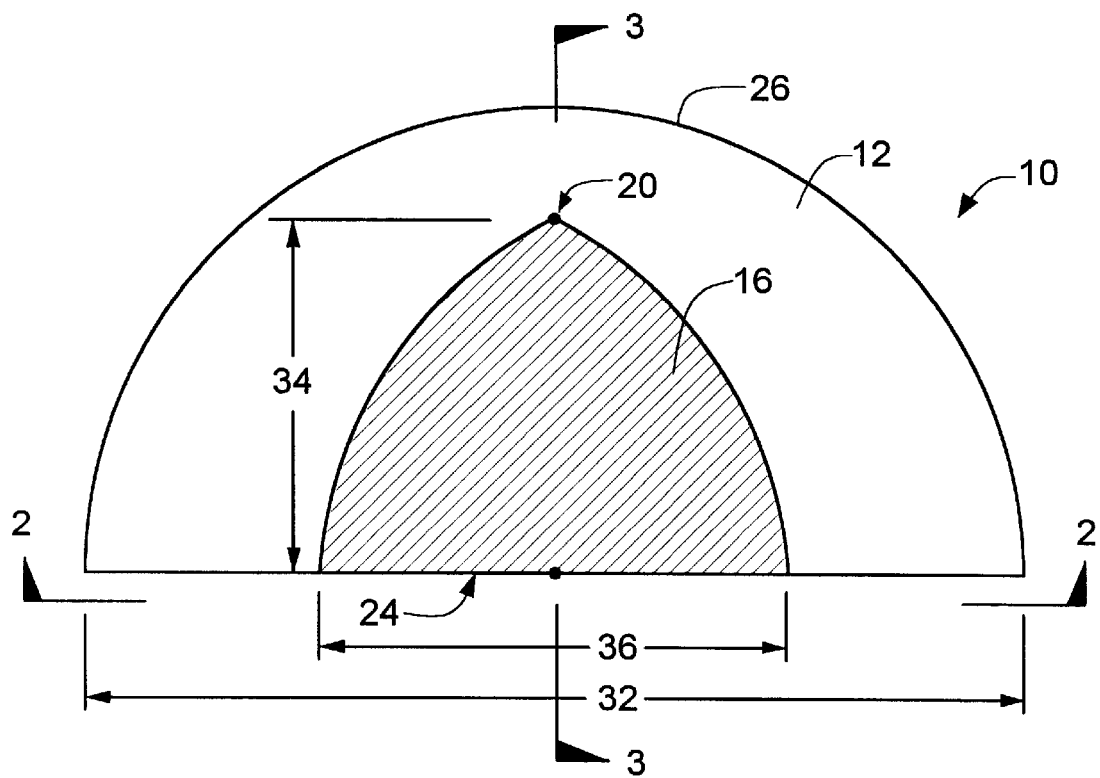
FIG. 1 schematically shows a plan view of a breast supporting apparatus manufactured in accordance with a preferred embodiment of the invention.
Figure 2:
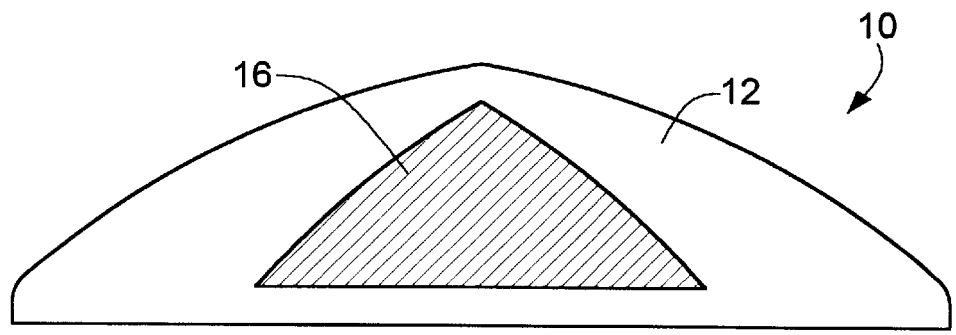
FIG. 2 schematically shows an elevational view of the breast supporting apparatus shown in FIG. 1 along the line 2—2.
Figure 3:
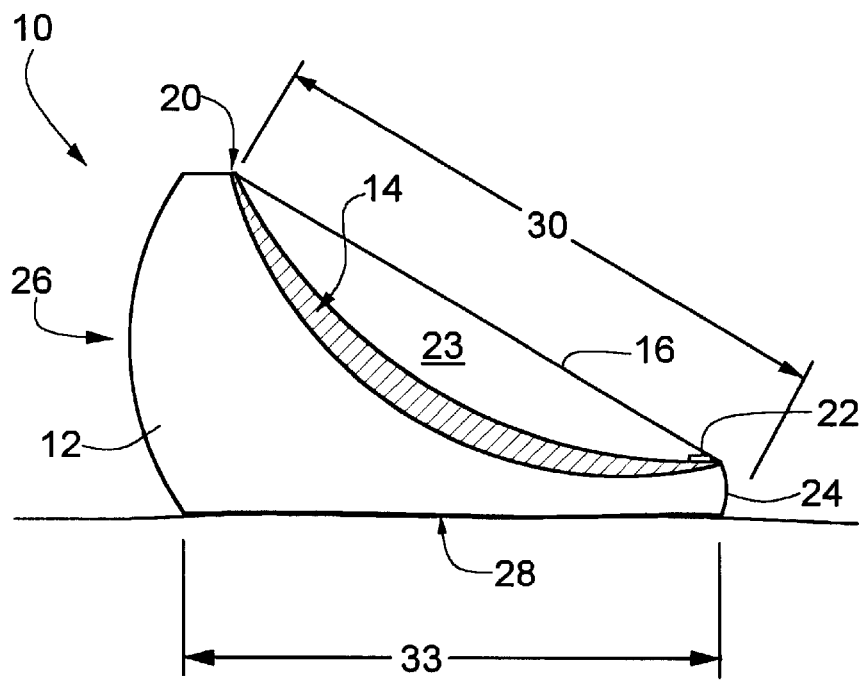
FIG. 3 schematically shows a cross-sectional view of the breast supporting apparatus shown in FIG. 1 along line 3—3.

FIGS. 1–3 schematically show a breast supporting apparatus ("breast pillow 10") manufactured in accordance with a preferred embodiment of the invention. In particular, the breast pillow 10 includes a body 12 having a recessed supporting surface ("supporting surface. 14") for supporting a person's breast, and a flap 16 having a strip of coupling fabric ("fabric strip 18") and connected to the supporting surface 14. The flap 16 is connected to the supporting surface 14 to form a hinge 20.

The supporting surface 14 also includes a fastener 22 such as, for example, a VELCRO™ strip, to couple with the coupling fabric strip 18 on the flap 16. Alternatively, the flap 16 may be manufactured from a material that readily couples with the VELCRO™ strip, thus eliminating the need for the fabric strip 18. When coupled, the supporting surface 14 and the flap 16 together define a re-closable chamber 23 for receiving and containing a heat absorbing apparatus. The heat absorbing apparatus preferably is a conventional ice bag (discussed below).

In preferred embodiments, the body 12 of the breast pillow 10 is crescent shaped and has rounded corners and edges. The body 12 further includes an interior that may be stuffed with any known filler material, such as conventional cotton based stuffing. Moreover, it is preferred that the flap 16 and body 12 be manufactured from the same woven fabric materials to reduce manufacturing costs. The flap 16 thus may be considered to be integral to the body 12 via the hinge 20. Since it is expected to be used in medical applications, such as after breast surgery, the fabric materials preferably are hypo-allergenic. The flap 16 also can include a thin padded layer (not shown) to further insulate the breast from contact with the heat absorbing apparatus within the chamber 23.

The breast pillow 10 further includes a front surface 24, and a rear surface 26 that is much larger than the front surface 24. When in use, the front surface 24 may be positioned against the base of the breast while the top of the rear surface 26 further supports the breast. The breast pillow 10 also includes a bottom surface 28 that supports the body 12 against a base surface. The base surface may be, for example, a bed or a sofa that also is supporting the person. In alternative embodiments, the bottom surface 28 of the body 12 may include rubber material to provide a frictional resistance against the supporting base. This frictional resistance should limit movement of the base during use.

The breast pillow 10 preferably is sized small enough so that it is not unduly cumbersome, and yet large enough to provide the desired function. In preferred embodiments, the front surface 24 extends about 0.5 inches from the bottom surface 28, the rear surface 26 extends about 3.5 inches from the bottom surface 28, the flap 16 has a flap length 30 of about 6.0 inches, and the bottom surface 28 has a bottom length 32 of about 12.0 inches and a bottom width 33 of about 5.5 inches. The recess similarly preferably has a recess width 34 of about 4.5 inches and a recess length 36 of about 6.0 inches. These-dimensions may be modified, however, depending upon the size of the person using the breast pillow 10. For example, the breast pillow 10 can be sized in standard small, medium, and large sizes. Each size may be color coded to readily distinguish the size of each breast pillow 10.

Figure 4:
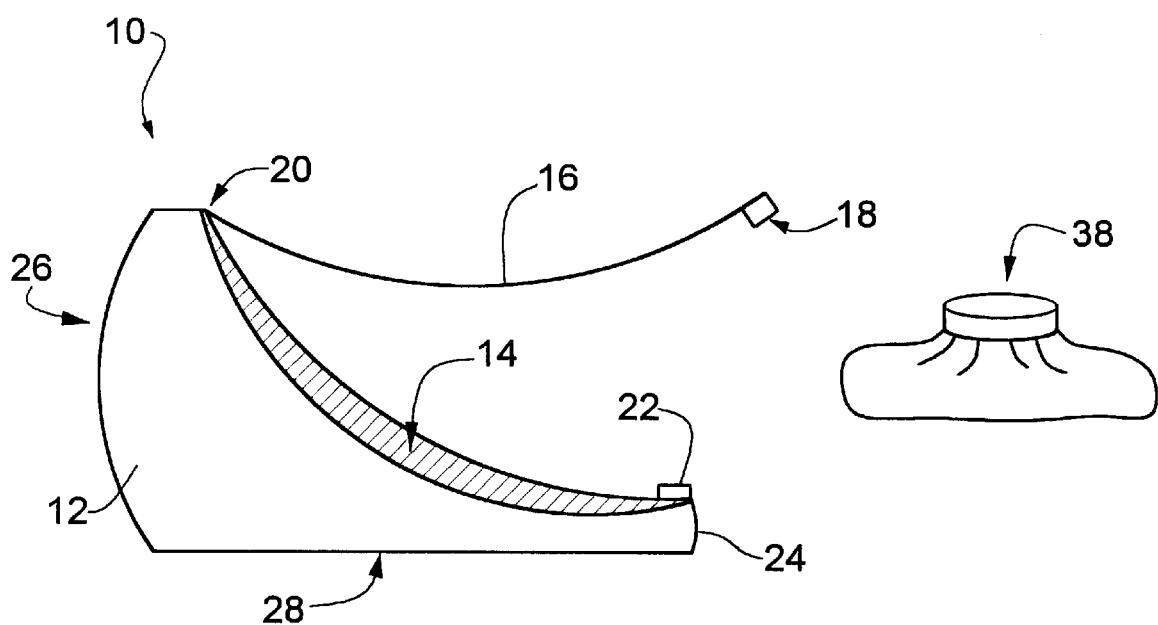
FIG. 4 schematically shows a cross-sectional view of the breast supporting apparatus shown in FIG. 1 with an ice bag that is to be disposed in the apparatus.

FIG. 4 schematically shows a cross-sectional view of the breast pillow 10 shown in FIG. 1 with an ice bag 38 or cold compress 38 about to be disposed in the chamber 23. The cold compress 38 may be any conventionally known cold compress 38 such as, for example, a CRYOTHERM™ cold/hot gel pack, available from Corflex Incorporated of Melrose, Mass. Alternatively, any other appropriately sized heat absorbing apparatus may be used such as, for example, a cold compress.

Figure 5:
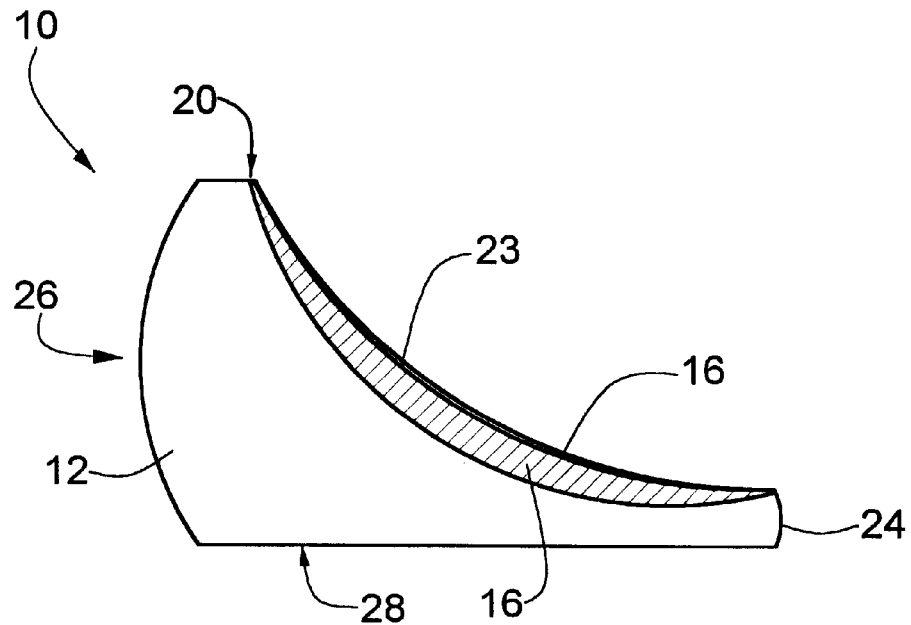
FIG. 5 schematically shows a cross-sectional view of an alternative embodiment of the breast supporting apparatus.

In preferred embodiments, the flap 16 is sized so that its interior surface rests against the supporting surface 14 when no heat absorbing apparatus is within the chamber 23. Accordingly, the chamber 23 may be considered to be an expandable chamber 23 that may have substantially a zero volume when it contains nothing. FIG. 5 shows such a flap 16, which enables a person to effectively use the breast pillow 10 without the heat absorbing apparatus. In other embodiments (e.g., that shown in FIGS. 1–3), the flap 16 is sized to be relatively taut across the recess of the supporting surface 14 to ensure that the chamber 23 always has a non-zero volume.

Figure 6:
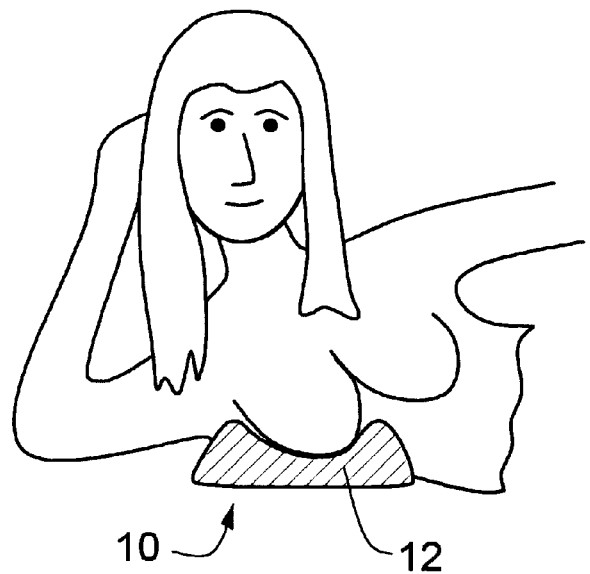
FIG. 6 schematically shows use of the breast supporting apparatus shown in FIG. 1.

FIG. 6 shows use of a preferred embodiment of the invention. In use, it first may be determined whether a heat absorbing apparatus is necessary or desirable. If so, then the flap 16 is lifted to open the chamber 23 and a heat absorbing apparatus is inserted into the chamber 23. The flap 16 then is closed (by coupling the fastener 22 and fabric strip 18) to close the chamber 23 and substantially contain the heat absorbing apparatus. The breast pillow 10 then should be positioned underneath the person's breast when laying on her side so that the flap 16 contacts the breast.

If a heat absorbing apparatus is not necessary or desired, then the breast pillow 10 is positioned underneath the person's breast when laying on her side. In such case, it is not necessary that the flap 16 be coupled to the body 12. Although VELCRO™ and a strip of fabric have been shown herein to secure the flap 16, it should be noted that any conventionally known securing mechanism may be used to couple the flap 16 and the body 12. For example, zippers or buttons may be utilized.

In alternative embodiments, the breast pillow 10 may be manufactured from other relatively soft materials. For example, a foam-based material, such as neoprene, may be used in lieu of fabric and stuffing. It is expected that use of such material would require different manufacturing processes than those used for fabric and stuffing based breast pillows 10.

Accordingly, the breast pillow 10 both supports the breast while also providing the anti-inflammatory function if a heat absorbing apparatus is contained in the chamber 23. Both functions are provided in a less cumbersome and more efficient manner than that known in the prior art. In addition, preferred embodiments of the breast pillow 10 are relatively simple and inexpensive to manufacture.

Although various exemplary embodiments of the invention have been disclosed, it should be apparent to those skilled in the art that various changes and modifications can be made which will achieve some of the advantages of the invention without departing from the true scope of the invention. These and other obvious modifications are intended to be covered by the appended claims.

I claim:

1. A pillow for supporting an extremity of a person, the pillow comprising:

a body having a support surface for supporting the extremity, the support surface defining a recessed surface and including a fastener; and a flap connected to the support surface and including a coupler to removably couple with the fastener on the support surface, the flap and recessed surface defining a chamber when the coupler is coupled to the fastener.

2. The pillow as defined by claim 1 wherein the body defines an interior for containing stuffing material.

3. The pillow as defined by claim 1 wherein the body is substantially crescent shaped.

4. The pillow as defined by claim 1 wherein the body is comprised of fabric.

5. The pillow as defined by claim 1 wherein the body and flap are comprised of the same material.

6. The pillow as defined by claim 1 wherein the body includes a bottom surface for supporting the body, the bottom surface being substantially flat.

7. The pillow as defined by claim 1 wherein the fastener is comprised of VELCRO™.

8. The pillow as defined by claim 1 wherein the body includes a front surface and a rear surface, the rear surface being larger than the front surface.

9. The pillow as defined by claim 1 wherein the chamber is adapted to contain a heat absorbing apparatus.

10. The pillow as defined by claim 1 wherein the recessed surface is substantially concave.

11. The pillow as defined by claim 1 wherein the chamber is expandable from a substantially zero volume.

12. A pillow for supporting an extremity of a person, the pillow comprising:

a body having a supporting surface for supporting the extremity, the supporting surface defining a recessed surface and having a fastener; and a flap connected to the supporting surface and having means for defining a chamber between the flap and the supporting surface, the flap being removably couplable with the fastener.

13. The pillow as defined by claim 12 wherein the defining means includes a fastener connected to the supporting surface and a coupler on the flap to couple the flap to the fastener.

14. The pillow as defined by claim 12 wherein the body defines an interior for containing stuffing material.

15. The pillow as defined by claim 12 wherein the body is substantially crescent shaped.

16. The pillow as defined by claim 12 wherein the body and flap are comprised of the same material.

17. The pillow as defined by claim 12 wherein the recessed surface is substantially concave.

* * * * *